United States Patent
Wiesel

(10) Patent No.: US 7,680,532 B2
(45) Date of Patent: Mar. 16, 2010

(54) DETECTING ATRIAL FIBRILLATION, METHOD OF AND APPARATUS FOR

(76) Inventor: Joseph Wiesel, 484 Duryea Ter., West Hempstead, NY (US) 11552

( * ) Notice: Subject to any disclaimer, the term of this patent is extended or adjusted under 35 U.S.C. 154(b) by 1066 days.

(21) Appl. No.: 11/355,050

(22) Filed: Feb. 15, 2006

(65) Prior Publication Data

US 2006/0195037 A1    Aug. 31, 2006

Related U.S. Application Data

(60) Provisional application No. 60/656,310, filed on Feb. 25, 2005.

(51) Int. Cl.
*A61B 5/04* (2006.01)
(52) U.S. Cl. .......................... 600/518; 607/4
(58) Field of Classification Search ............... 600/508, 600/509, 518; 607/4, 5, 6, 14
See application file for complete search history.

(56) References Cited

U.S. PATENT DOCUMENTS

| | | | |
|---|---|---|---|
| 4,260,951 A | 4/1981 | Lewyn | |
| 4,621,643 A | 11/1986 | New, Jr. et al. | |
| 4,685,464 A | 8/1987 | Goldberger et al. | |
| 4,700,708 A | 10/1987 | New, Jr. et al. | |
| 5,113,869 A | 5/1992 | Nappholz et al. | |
| 5,117,834 A | 6/1992 | Kroll et al. | |
| 5,228,449 A | 7/1993 | Christ et al. | |
| 5,342,404 A | 8/1994 | Alt et al. | |
| 5,456,261 A | 10/1995 | Luczyk | |
| 5,471,991 A | 12/1995 | Shinnar | |
| 5,609,158 A | 3/1997 | Chan | |
| 5,626,143 A | 5/1997 | Meyer, III | |
| 5,772,604 A | 6/1998 | Langberg et al. | |
| 5,842,997 A | 12/1998 | Verrier et al. | |
| 5,941,831 A | 8/1999 | Turcott | |
| 6,095,984 A | 8/2000 | Amano et al. | |
| 6,126,595 A | 10/2000 | Amano et al. | |
| 6,249,700 B1 | 6/2001 | Alt | |
| 6,327,499 B1 | 12/2001 | Alt | |
| 6,519,490 B1 * | 2/2003 | Wiesel | 600/518 |

OTHER PUBLICATIONS

Joseph Wiesel et al "The Use of a Modified Sphygmomanometer to Detect Atrial Fibrillation in Outpatients", PACE, vol. 27 (May 2004).
Braunwald'S A Textbook of Cardiovascular Medicine, 7th Edition, 2005, pp. 817, 840.
Degown'S Diagnostic Examination, 8th Edition, 2004, p. 362.

* cited by examiner

*Primary Examiner*—Carl H Layno
*Assistant Examiner*—Brian T Gedeon
(74) *Attorney, Agent, or Firm*—Davidoff Malito & Hutcher LLP

(57) ABSTRACT

A method and apparatus to determine possible atrial fibrillation or absence of atrial fibrillation that includes detecting pulse rhythms from a succession of time intervals each corresponding to a respective interval of time between successive pulse beats; analyzing the detected pulse rhythms to make a determination of possible atrial fibrillation; indicating the possible atrial fibrillation from the determination; or making a determination of the absence of atrial fibrillation.

17 Claims, 9 Drawing Sheets

DETECTING ATRIAL FIBRILLATION, METHOD OF AND APPARATUS FOR

CROSS-REFERENCE TO CO-PENDING PATENT APPLICATION

This application claims priority from U.S. Provisional Patent Application Ser. No. 60/656,310, filed Feb. 25, 2005.

BACKGROUND OF THE INVENTION

1. Field of the Invention

The present invention generally relates to a method of and an apparatus for detecting atrial fibrillation by monitoring and analyzing pulse beats using an algorithm that can exclude many rhythm abnormalities that are not atrial fibrillation.

2. Discussion of the Related Art

The heart is the major muscle that functions as the primary pump for blood flow throughout the body. The heart contains two upper chambers called atria and two lower chambers called ventricles. The right atrium receives oxygen-depleted blood while the left atrium receives blood enriched with oxygen from the lungs. When the atria are full, the outlet valves within the heart open and the atria squeeze blood into the ventricles. The right ventricle then pumps oxygen-depleted blood to the lungs while the left ventricle pumps oxygen-enriched blood to all parts of the body. In this fashion, the heart functions primarily as a double sided pump.

The heart's internal pacemaker, known as the sinus node, signals the start of each heart beat. This signal originates in the right atrium in the sinoatrial node and travels simultaneously to the left atrium and down to the interatrial septum to the atrioventricular node. The cycle of electrical stimulation that normally occurs is referred to as normal sinus rhythm. The contraction of the ventricles will be referred to as the heart beats.

Many rhythm abnormalities may be present. Atrial fibrillation is one rhythm abnormality in which the atria do not contract normally. Instead, there is a continuously varying pattern of electrical activation of the atria resulting in a rapid highly irregular pattern of impulses reaching the atrioventricular node. The atrioventricular node acts as a filter and allows a reduced number of these impulses to reach the ventricles which results in a highly irregular heartbeat pattern. This irregular pattern has been shown in previous studies to be a random pattern (Bootsma et al: Analysis of R-R Intervals in Patients with Atrial Fibrillation at Rest and During Exercise. Circulation 41: 783, 1970). Whenever the term "irregular' is used in this application it refers to this random pattern of beats found almost exclusively in atrial fibrillation.

Atrial fibrillation is one of the most common arrhythmias requiring medical attention. Atrial fibrillation may be caused by a number of heart conditions, such as angina, myocardial infarction, heart valve abnormalities, and high blood pressure. These conditions may stretch or scar the atria, thereby causing irregularities in the heart system. Atrial fibrillation may also accompany lung problems or thyroid gland disorders and is also associated with significant morbidity and possible mortality. All persons, young and old, female or male, including the visually and/or sight impaired, may experience atrial fibrillation.

Atrial fibrillation may occur intermittently or chronically. The most serious complication of atrial fibrillation is formation of a blood clot in the left atrium which may result in a stroke. Many people who develop atrial fibrillation, however, are unaware of their abnormal rhythm. Some in the medical profession have, therefore, advocated self screening of the pulse to detect for the possible occurrence of atrial fibrillation. The literature, however, is generally limited to disclosing instructions for manually taking one's pulse accompanied with additional descriptive information.

The reason for using the pulse to detect atrial fibrillation is that the pulse usually corresponds to the heartbeat. The contraction of the left ventricle ejects blood from the heart into the aorta and the resulting pressure wave is detected as a pulse in the arterial system. However, when atrial fibrillation is present, the amount of time between beats varies irregularly.

With a longer time interval between beats, there is more time to fill the ventricles with blood and more blood is ejected by the ventricle in the beat following this long interval. This larger volume of blood in the aorta results in a higher systolic pressure for that beat.

Conversely, when the time interval between beats is short, there is less time for ventricular filling and the volume of blood ejected in the beat following the short time interval is less. This results in a lower systolic pressure for that beat. In some cases, the time interval between beats is so short that the systolic pressure of the following beat is so low that it cannot be palpated as a pulse. A ventricular contraction that cannot be palpated as a pulse in the arterial system results in what is called a "pulse deficit." This is very common in atrial fibrillation. This pulse deficit means that an irregular pattern of heartbeats in the ventricle may result in a less irregular pulse beat pattern since the shortest intervals between heartbeats may not be detected in the pulse. Therefore, any method used to determine the presence of atrial fibrillation by analyzing the time intervals between beats in the ventricles may not be valid when applied to the pulse beats.

An article by Bert K. Bootsma, Adriann J. Hoelen, Jan Strackee and Frits L. Meijler, entitled Analysis of R-R Intervals in Patients with Atrial Fibrillation at Rest and During Exercise, Circulation, Volume XLI, May 1970 describes an analysis of the time intervals between ventricular contractions using the electrocardiogram. The article evaluates the standard deviation divided by the mean of the time intervals between ventricular beats in normal subjects and in those with atrial fibrillation. The article finds that atrial fibrillation can be accurately differentiated from normal sinus rhythm using this formula. However, this was based on ventricular contractions determined by the electrocardiogram and was not applied to the pulse beat intervals.

Due to the presence of a pulse deficit in atrial fibrillation, results based on ventricular contractions determined by the electrocardiogram may not apply to time intervals determined from analyzing the pulse. Furthermore, the extent of the pulse deficit depends on the method used to determine the pulse beats. A method which detects only pulse beats with high systolic pressures will detect fewer pulse beats compared to a more sensitive method. The more sensitive techniques may be better for detecting more pulse beats but they may also give more false positive readings.

For example, with a photoplethysmograph using a finger probe with a light source and a photoelectric detector, when the sensitivity of the device is increased, the slightest finger movement is detected as a pulse beat. This device at the highest sensitivity setting detects an irregular pulse in those with normal sinus rhythm due to random noise from finger movement. At the highest sensitivity setting, this device would not be useful to detect atrial fibrillation in the home setting. At the lowest sensitivity setting, very few pulse beats would even be detected. Therefore, any device and algorithm which uses the pulse to detect atrial fibrillation must be designed specifically for the purpose of detecting atrial fibrillation.

Other rhythm abnormalities that are not associated with an increased risk of stroke are found very commonly. For example, premature atrial contractions or premature ventricular contractions are found in many people, even those with no heart conditions. These rhythm abnormalities are intermittent but they are found much more commonly than atrial fibrillation and generally do not require treatment. Therefore, a device that is designed to detect atrial fibrillation should include an algorithm that would not detect premature beats as an irregular rhythm. If a device designed to detect atrial fibrillation does not include an algorithm to reduce the detection of premature beats, the number of false positive readings would be very high and the device would be of very limited value. Those who might use such a device on a regular basis to detect asymptomatic atrial fibrillation would quickly stop using this device if the vast majority of abnormal readings turn out to be due to premature beats and not atrial fibrillation.

U.S. Pat. No. 6,485,429 describes a method and apparatus that can detect arrhythmia using an oscillometric blood pressure monitor. This patent discloses a method for detecting multiple rhythm abnormalities including supraventricular premature contractions, ventricular premature contractions, atrial fibrillation, paroxysmal supraventricular tachycardia, sinus tachycardia, and ventricular bradycardia. A study performed by the inventor of the patent using a commercially manufactured embodiment of the patent found that the device only detected 66.6% of patients with atrial fibrillation while detecting 85.7% of premature ventricular contractions (Forstner K W, American Society of Hypertension 16th Annual Meeting 2003, page 25). Premature ventricular contractions are found much more commonly than atrial fibrillation. Therefore a device that has a very high rate of detecting premature ventricular contractions and a significantly lower rate of detecting atrial fibrillation would not be a very useful device if the goal is to detect atrial fibrillation exclusively.

Other patents that can detect rhythm abnormalities would also be subject to very high false positive rates if they are used to detect atrial fibrillation. U.S. Pat. No. 6,095,984 describes an embodiment (section 1-2-1) where a pulse variation over 0.5% would be detected as abnormal. The most common rhythm abnormality, sinus arrhythmia, by definition (Braunwald, E. Heart Disease A textbook of Cardiovascular Medicine 1992, p 674) has a heart rate that varies by more than 10%. U.S. Pat. No. 6,095,984 did not describe methods and apparatus to look for atrial fibrillation and would not be useful for home monitoring of atrial fibrillation, because the algorithm can result in multiple sources of false readings and the apparatus was not specifically set for optimal detection of pulse beats in atrial fibrillation.

An algorithm designed to detect atrial fibrillation by the irregularity of the pulse beat intervals should be designed to reduce the effects of premature beats. One method of reducing the effect of premature beats is to limit the number of beats used in determining the irregularity of the pulse intervals. For example, if premature beats occur on average every twenty beats, then limiting the analysis to only ten beats would reduce the likelihood of a premature beat occurring during the period being analyzed. This method was used in a trial and published in Wiesel et al, PACE, 27:639-643 (2004). In this study, the rhythm of 450 outpatients of which 54 were documented to have atrial fibrillation was analyzed. The study used an algorithm that calculated the irregularity index, defined as the standard deviation of the time intervals between beats divided by the mean of the time intervals between beats, and analyzed only the last ten beats recorded by an automatic oscillometric blood pressure monitor. All recordings with an irregularity index greater than 0.06 were considered to be irregular. This study found that 100% of patients with atrial fibrillation were detected while 16% of patients without atrial fibrillation were also found to be irregular (sensitivity for detecting atrial fibrillation 100%, specificity 84%). This is a marked improvement in the rate of detecting atrial fibrillation over the method used by Forstner.

Though the sensitivity for detecting atrial fibrillation using the irregularity index applied to the last ten beats recorded by an automatic blood pressure monitor is excellent, there is room for improvement in specificity. Premature beats are common rhythm abnormalities that can reduce the specificity of the irregularity index. For example, a ventricular premature beat occurs earlier than the normal beats but results in a pause following the beat. A premature beat usually results in a lower pulse pressure than the normal beats. This premature beat with its lower pulse pressure would often not be recorded by the blood pressure monitor at all. As a result of this premature beat, there would be a pause equal to the time interval between two normal beats. For a patient with a heart rate of 60 beats per minute, the pulse interval would be one second between normal beats. A premature ventricular beat would result in a pulse interval of two seconds as measured by a blood pressure cuff. The irregularity index for nine time intervals between beats of one second and one interval of two seconds due to one premature ventricular beat would be equal to 0.29, well above the threshold value of 0.06. If the premature beat occurs 0.5 seconds following a normal beat and it is detected by the blood pressure monitor, then there will be a short interval followed by a long interval. With eight intervals of one second, one interval of 0.5 seconds and one interval of 1.5 seconds, the irregularity index would be 0.24, still very abnormal.

U.S. Pat. No. 6,519,490 issued to Joseph Wiesel discloses a method to reduce the impact of premature beats by deleting only those beats that occur at shorter intervals than the mean beat to beat interval. This method was found to somewhat improve the specificity of an automatic blood pressure monitor used to detect atrial fibrillation. However, an algorithm that can recognize when a premature beat occurs and that eliminates both the short intervals and the long intervals associated with these beats could further reduce the false positive rate and improve the specificity for the blood pressure monitors used to detect atrial fibrillation. Some patients have very frequent premature beats occurring every other beat. In that case, all the time intervals are either shorter or longer than the mean of the time intervals. If all the beats are eliminated because they fall outside the upper and lower threshold values around the mean time interval then that pattern is not typical of atrial fibrillation and will be considered a regular rhythm. Atrial fibrillation has continuously varying time intervals around the mean time interval such that there are usually at least a few time intervals near the mean time interval that will not be eliminated by this algorithm.

Occasionally, premature beats will occur frequently with varying intervals. For example, if the normal beats occur at time intervals of one second, there may be premature beats occurring at 0.5 second, 0.75 second and 0.85 second all in the same patient during the period of time recorded by the blood pressure monitor. If we eliminate some of these intervals because they exceed a threshold value, other intervals may still be present that can cause a high irregularity index. Another algorithm can be used to reduce the false positive rate for those patients with frequent premature beats. In atrial fibrillation there are no normal beats and having more than half of the time intervals almost exactly equal in length during the 10 to 40 seconds of a typical blood pressure monitor reading is unlikely. On the other hand, even with frequent premature beats, more than half the beats are usually normal beats. Thus, if we find that most of the time intervals are almost equal during one blood pressure reading, it is much more likely that this is not atrial fibrillation.

What is needed is a home monitoring method and apparatus to detect the possible presence of atrial fibrillation and communicate this condition to the user so that the user is alerted to consult a medical practitioner for further testing and/or treatment.

What is also needed is a method that can differentiate atrial fibrillation from a normal pulse pattern and from common heart rhythm abnormalities that are not of significant risk such as sinus arrhythmia, atrial premature beats and ventricular premature beats.

What is further needed is a method of and an apparatus for detecting irregular pulse rhythms during a time period and storing this information so that comparisons may be made with the pulse rate rhythms at later times.

What is further needed is a noninvasive and relatively simple method and apparatus that monitors pulse rate irregularities to detect atrial fibrillation, and that is suitable for use of all ages, and by the hearing and/or visually impaired and that is relatively easy to use.

What is still further needed is a monitoring method and apparatus that detects the presence of irregular pulse beats and then displays and stores: i) the number of irregular pulse beats during a pre-selected time interval; and ii) the duration of time between beats during selected intervals.

Yet another need is for a monitoring method and apparatus that determine whether or not a pulse beat pattern is irregular based on algorithmic or heuristic operations performed on selected pulse beat data.

What is needed is a method and apparatus for detecting the presence of atrial fibrillation by detecting an irregular pattern of pulses using a sphygmomanometer.

What is needed is a method and apparatus for detecting the presence of atrial fibrillation by detecting an irregular pattern of pulses using a plethysmograph such as finger probe with a light source and photodetector.

BRIEF SUMMARY OF THE INVENTION

The present invention provides a method and apparatus that determines the presence of atrial fibrillation by (i) detecting the pulse beat intervals over a short time period to determine whether the intervals form a random, irregular pattern; (ii) determining whether this pulse beat pattern indicates possible atrial fibrillation and then; (iii) communicating this information to the user so that a medical practitioner may be consulted for further testing and/or treatment. The present invention also provides a method of and an apparatus for detecting irregular pulse rhythms during a time period and storing this information for comparison with the pulse rhythm at later time periods. The present invention may also detect patterns over multiple time periods and compare the patterns over various time periods.

The present invention further provides a noninvasive method of and an apparatus for monitoring the irregularity of the pulse beat pattern to detect atrial fibrillation. The invention may store and display information such as the number of irregular pulse beats during pre-selected time intervals and the duration of time between beats during the selected intervals. The invention also determines the presence of an irregular pulse beat pattern via algorithmic or heuristic operations performed on the relevant data.

Pulse beats may be monitored by use of an inflatable cuff wrapped around a person's appendage, such as an arm, which detects the pulse beats by either oscillometric or auscultatory means. The time intervals between pulse beats can be determined during cuff deflation or while the cuff is inflated at a fixed pressure.

The present invention allows for the elimination of at least one or more of the pulse beat intervals detected during deflation of a blood pressure cuff if the time interval of the pulse beat is less than a minimal threshold value or greater than a maximum threshold value. This is necessary to prevent the detection of premature beats and to reduce the false positive rates for detecting atrial fibrillation.

The present invention allows for the detection of a normal rhythm if the percent of pulse intervals that fall within a narrow time period exceeds a threshold percent in order to detect normal sinus beats that may be interspersed with multiple other abnormal beats with varying pulse beat intervals.

Pulse beats may also be monitored through changes in light transmitted through various body appendages. Each pulse beat changes the light transmission through a location on the appendage. The change in the light transmission corresponds to a pulse beat and the time intervals between pulse beats may be determined.

Pulse beats may be monitored using other plethysmographic devices, ultrasound devices which measure arterial motion with each pulse beat, ultrasound doppler devices which detect blood flow within an artery or devices that rely on localized compression of the artery to detect the presence of a pulse beat. Using any of these techniques the time intervals between pulse beats can be determined.

A monitoring method of the present invention includes detecting irregular pulse beats, analyzing the irregularity based on one or more predetermined factors, and communicating this information to a user such as via a screen display, a paper printout, a tone, or auditory, vibratory or other sensory communication.

The invention may utilize algorithmic or heuristic techniques to determine whether the irregular pulse beats signal the possible presence of atrial fibrillation.

Other features and advantages of the present invention will become apparent from the following detailed description of the invention with reference to the accompanying drawings.

DETAILED DESCRIPTION OF THE INVENTION

One embodiment of the invention uses pulse beats that are detected using an inflatable cuff device. The inflatable cuff device may be a known apparatus used to measure blood pressure using oscillometric or auscultatory means.

The inflatable cuff device is placed around an appendage such as an arm and inflated above systolic pressure. While the cuff is deflated, the pulse beats are detected. The cuff deflation may be stopped and the cuff may remain at a fixed pressure to allow for monitoring of the pulse beats during a constant cuff pressure. The time of each pulse beat is delivered to a processor, which includes instructions that carry out the method described above.

Further, the processor stores the time of each pulse beat, the intervals between pulse beats and other information in a memory. The memory may include RAM or other device memory or include a hard disc, a floppy disk or other memory devices. The processor may comprise a microprocessor, and applications specific integrated circuit (ASIC), a programmable logic array (PLA) or reduced instruction set chip (RISC).

The processor determines from the pulse beat intervals if the pattern suggests atrial fibrillation or not. The processor then delivers the results to a printer, a display, a vibration generator, and/or an auditory generator, etc. which may include an indication that the pulse beat pattern is regular, irregular, in possible atrial fibrillation, or that a physician should be contacted. Other information, such as the pulse rate, may also be displayed.

This embodiment with an automatic sphygmomanometer that uses the oscillometric method for detecting the pulse beats and blood pressure was developed. To account for the pulse deficit at higher cuff pressures, and to account for possible respiratory variation in the systolic pressures of normal beats, and to reduce the influence of premature beats, an algorithm was developed that analyzed only the last ten beats detected during cuff deflation. The mean and standard deviation of these last ten beats was calculated and the quotient of the standard deviation over the mean was determined.

This was compared to a threshold value of 0.06. If the quotient was greater than the threshold value then the pulse pattern was determined to be irregular. As mentioned previously, this method was used in a trial and published in Wiesel et al, PACE, 27:639-643 (2004) using 450 outpatients of which 54 were documented to have atrial fibrillation. The sensitivity using this method with one blood pressure reading was 100% with a specificity of 84% for detecting atrial fibrillation.

Figure 3:
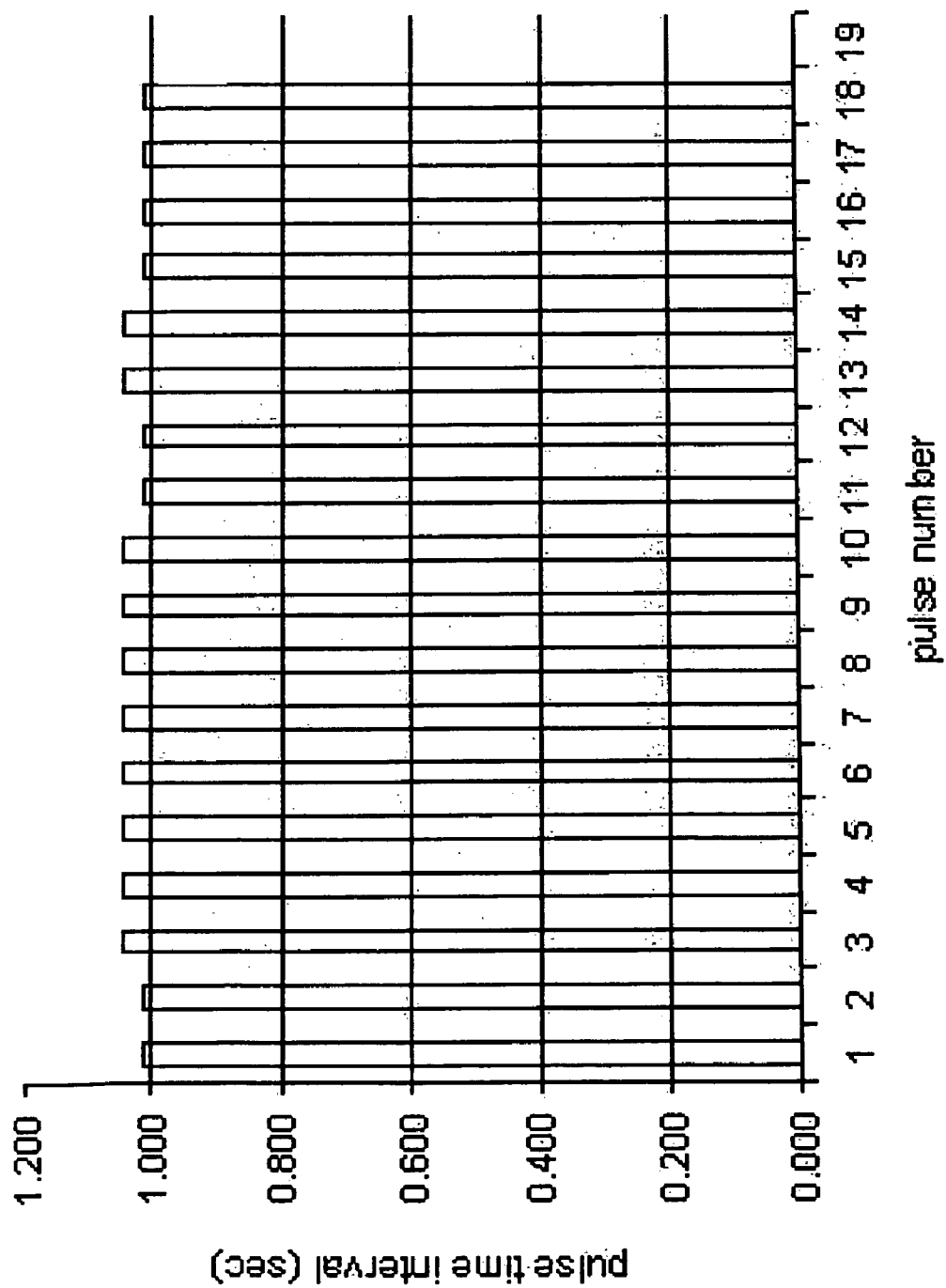
FIG. 3 is a graph showing pulse beat time intervals for regular sinus rhythm.
Figure 4:
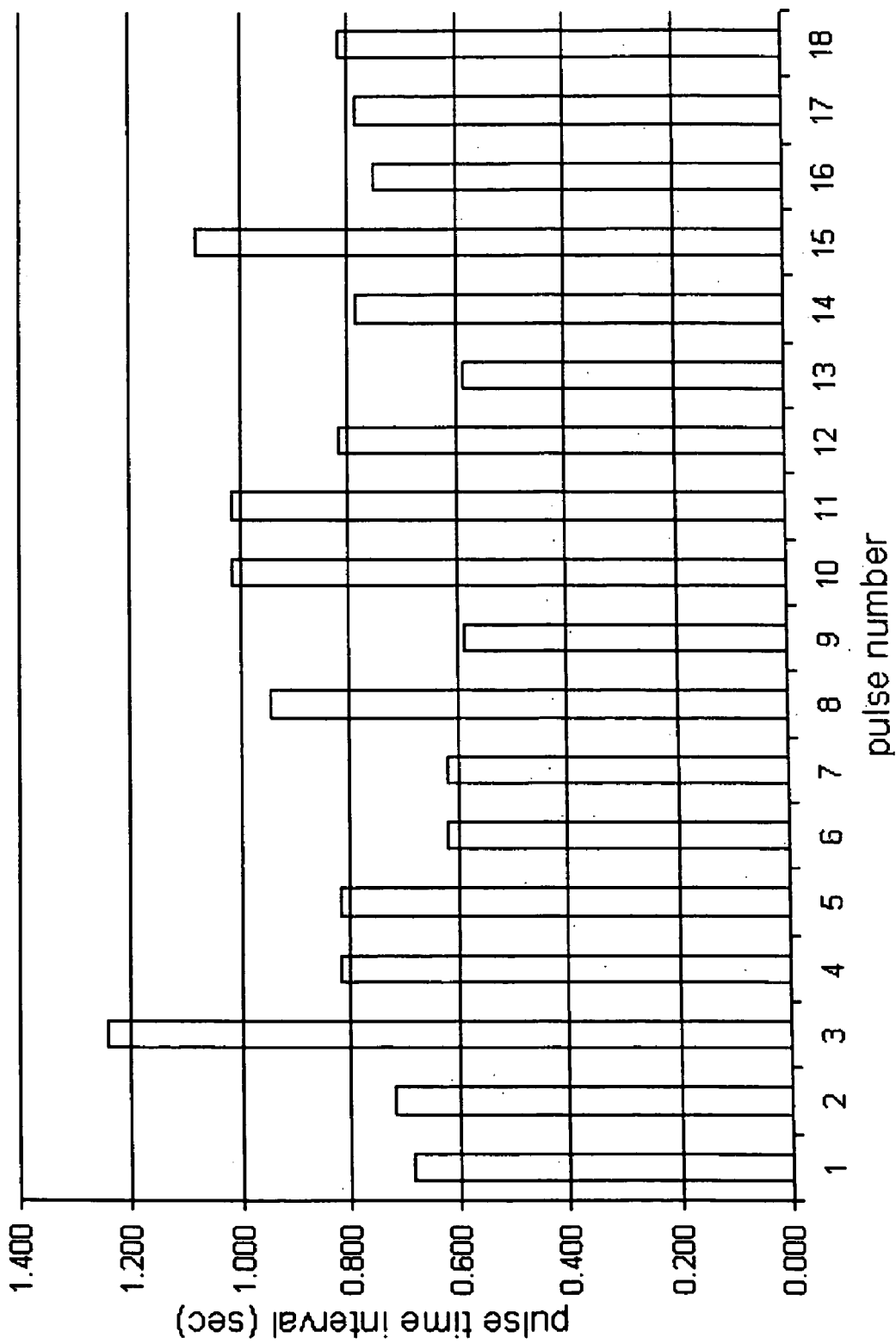
FIG. 4 is a graph showing pulse beat time intervals for atrial fibrillation.

All pulse time intervals recorded by the device are used to determine a mean time interval. For those readings found to be irregular one of two methods may be used to improve the specificity for atrial fibrillation. (See FIGS. 3 and 4).

Figure 1:
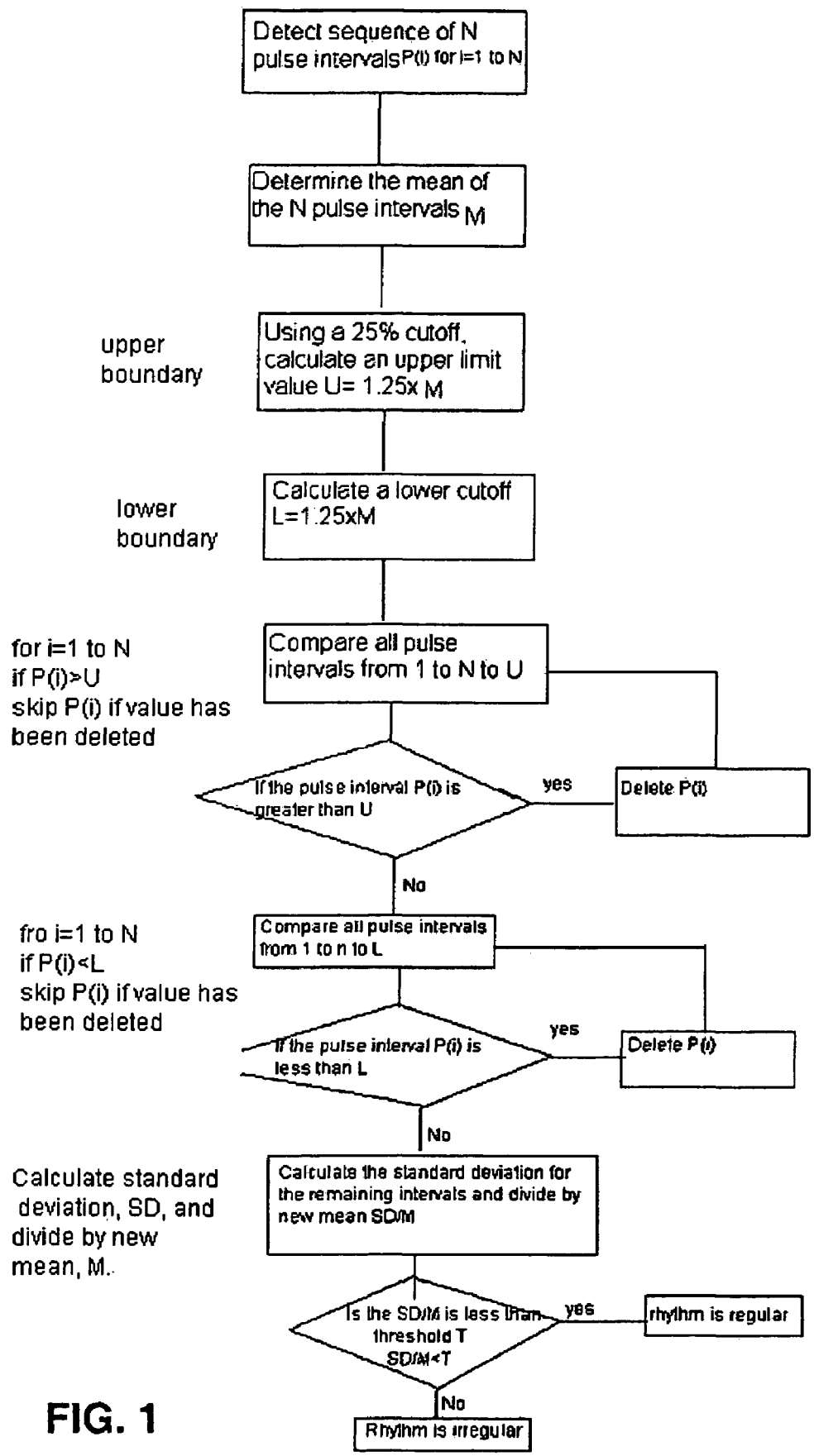
FIG. 1 is a flow chart of the algorithm (Algorithm I) for a first method of the present invention to determine possible atrial fibrillation.
Figure 5:
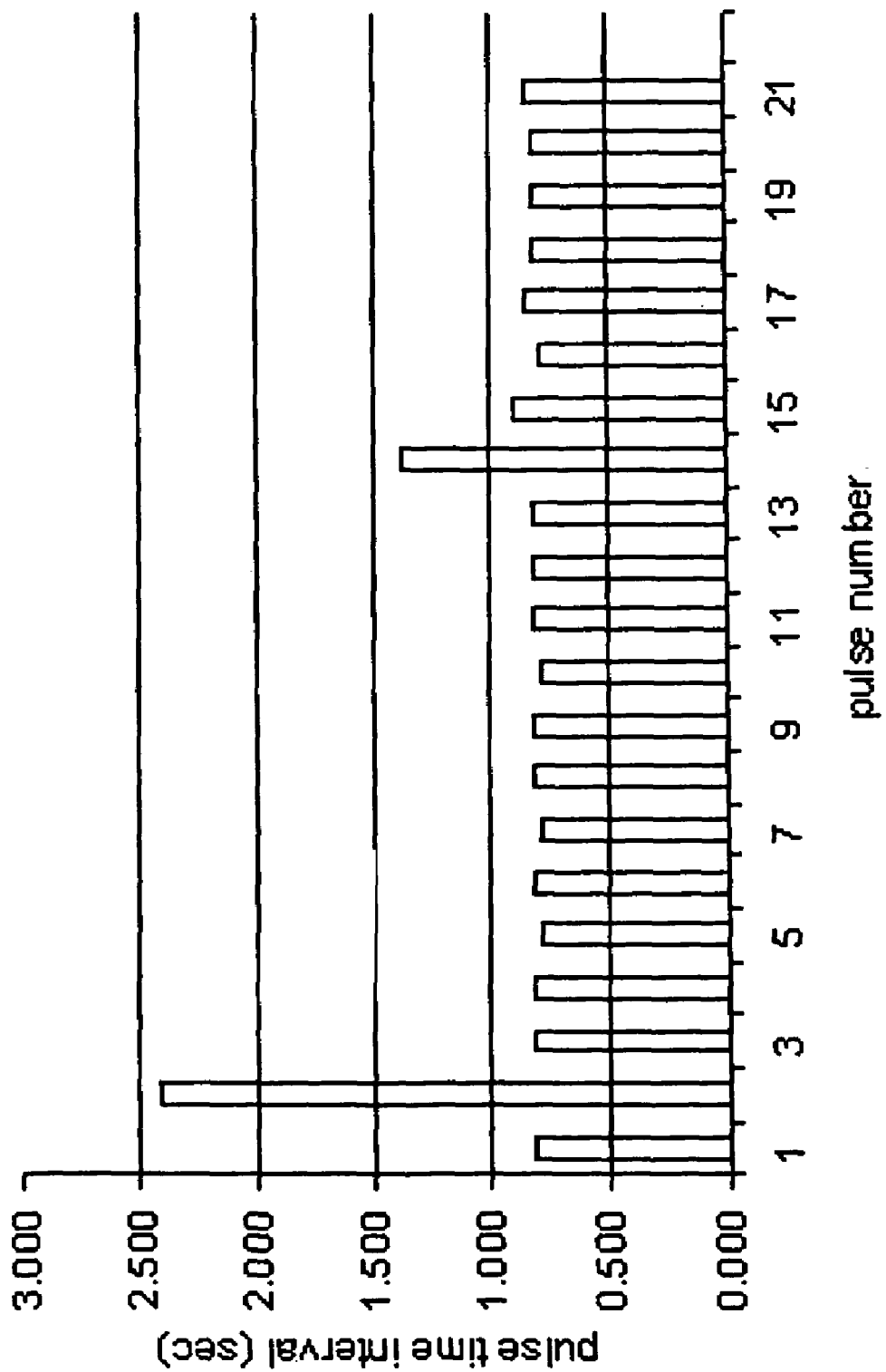
FIG. 5 is a graph showing pulse beat time intervals for sinus rhythm with premature beats, that were recorded as long time intervals, prior to application of Method I.
Figure 6:
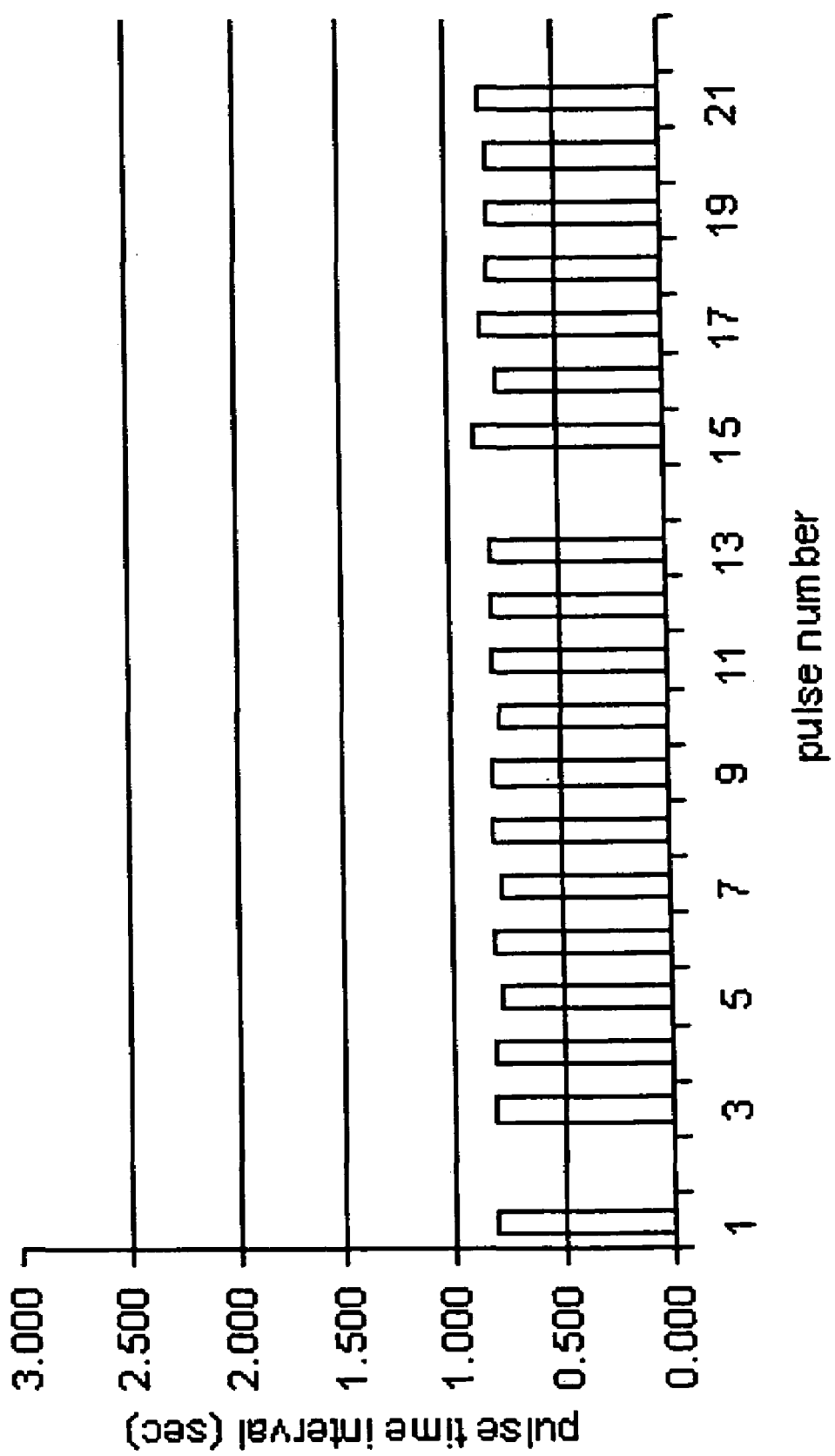
FIG. 6 is a graph showing pulse beat time intervals from graph 5 after application of Method I.

In a first preferred method of the present invention (FIG. 1), all recorded time intervals recorded by the automatic sphygmomanometer are used to determine a mean time interval. (See FIG. 5). All intervals more than about 25% above the mean (an upper boundary value) or less than about 25% below the mean (a lower boundary value) are eliminated. (See FIG. 6). The lower boundary value may be in a range of about 0.50 to about 0.90 times the mean and the upper boundary value may be in a range of 1.1 to 1.5 times the mean. The new mean and standard deviation are then calculated from the remaining time intervals. A new irregularity index is calculated as the ratio of the new standard deviation to the new mean. If the irregularity index is less than about 0.066 then the rhythm is considered regular. If the irregularity index is equal to or greater than about 0.066, then the rhythm is considered irregular and likely to be atrial fibrillation. If there are no time intervals remaining when those above or below the threshold values are eliminated, then the pattern is not consistent with atrial fibrillation and is typical of premature beats occurring every other beat. The rhythm is then considered regular. FIG. 1 is a flow chart schematic of the method described herein. Using this algorithm on the 247 irregular readings in the previously mentioned study (Wiesel et al, PACE, 27:639-643 (2004) resulted in all patients with atrial fibrillation continuing to be detected as irregular, but now approximately half of the previously irregular patients not in atrial fibrillation were reclassified as regular. This improved the specificity to around 92% while keeping the sensitivity at 100%.

Figure 2:
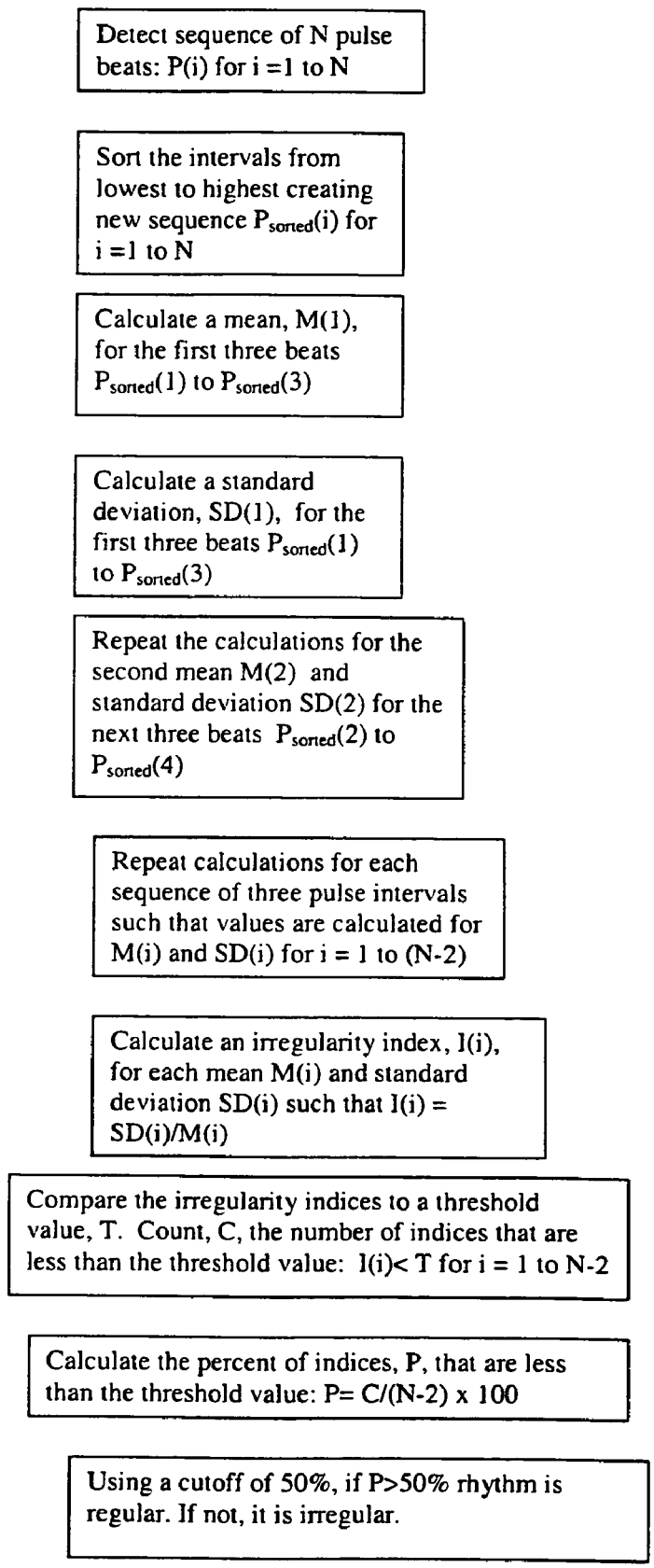
FIG. 2 is a flow chart of the algorithm (Algorithm II) for a second method of the present invention to determine possible atrial fibrillation.
Figure 7:
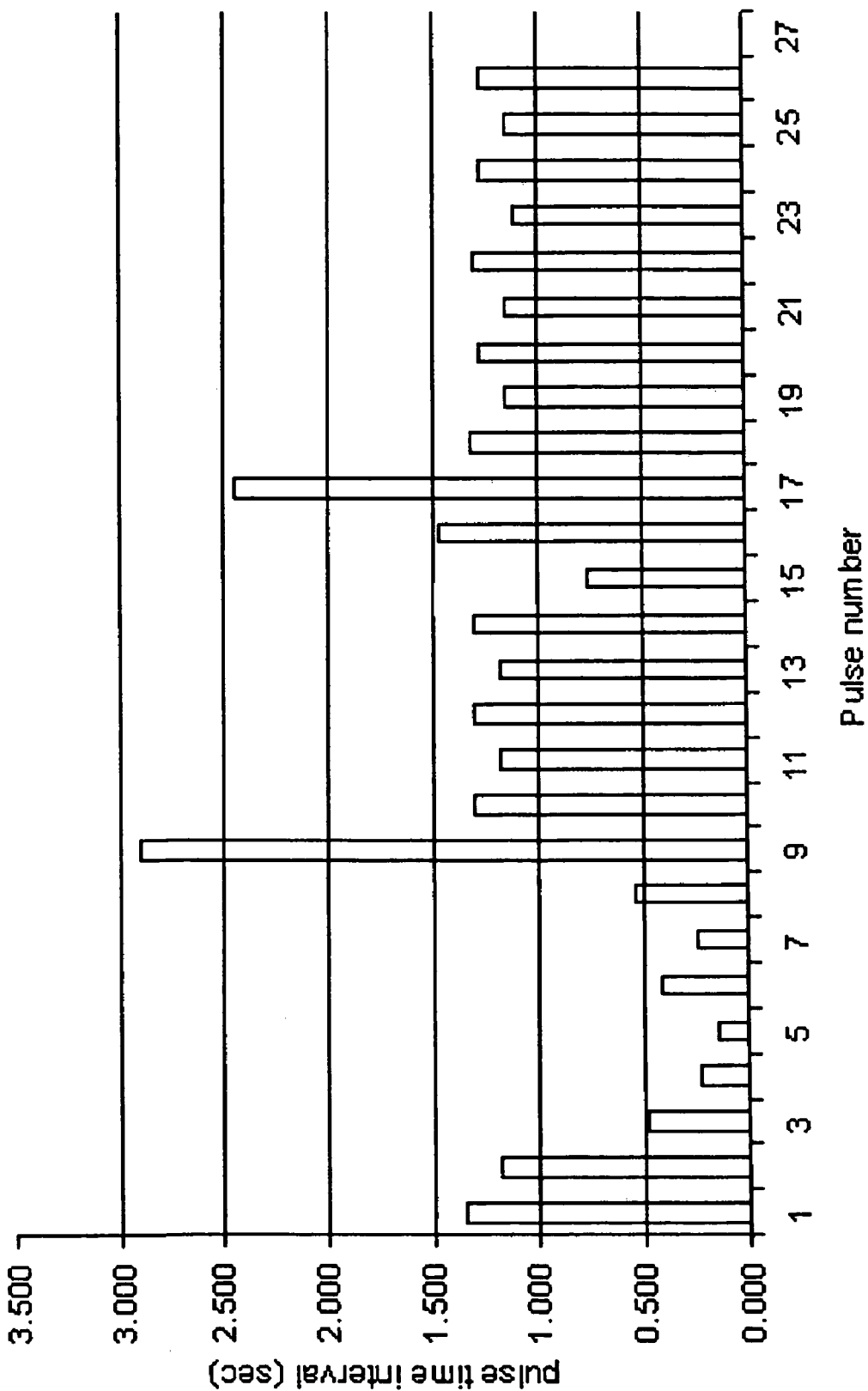
FIG. 7 is a graph showing pulse beat time intervals for sinus rhythm with frequent and varying premature beats recorded as both short and long time intervals.
Figure 8:
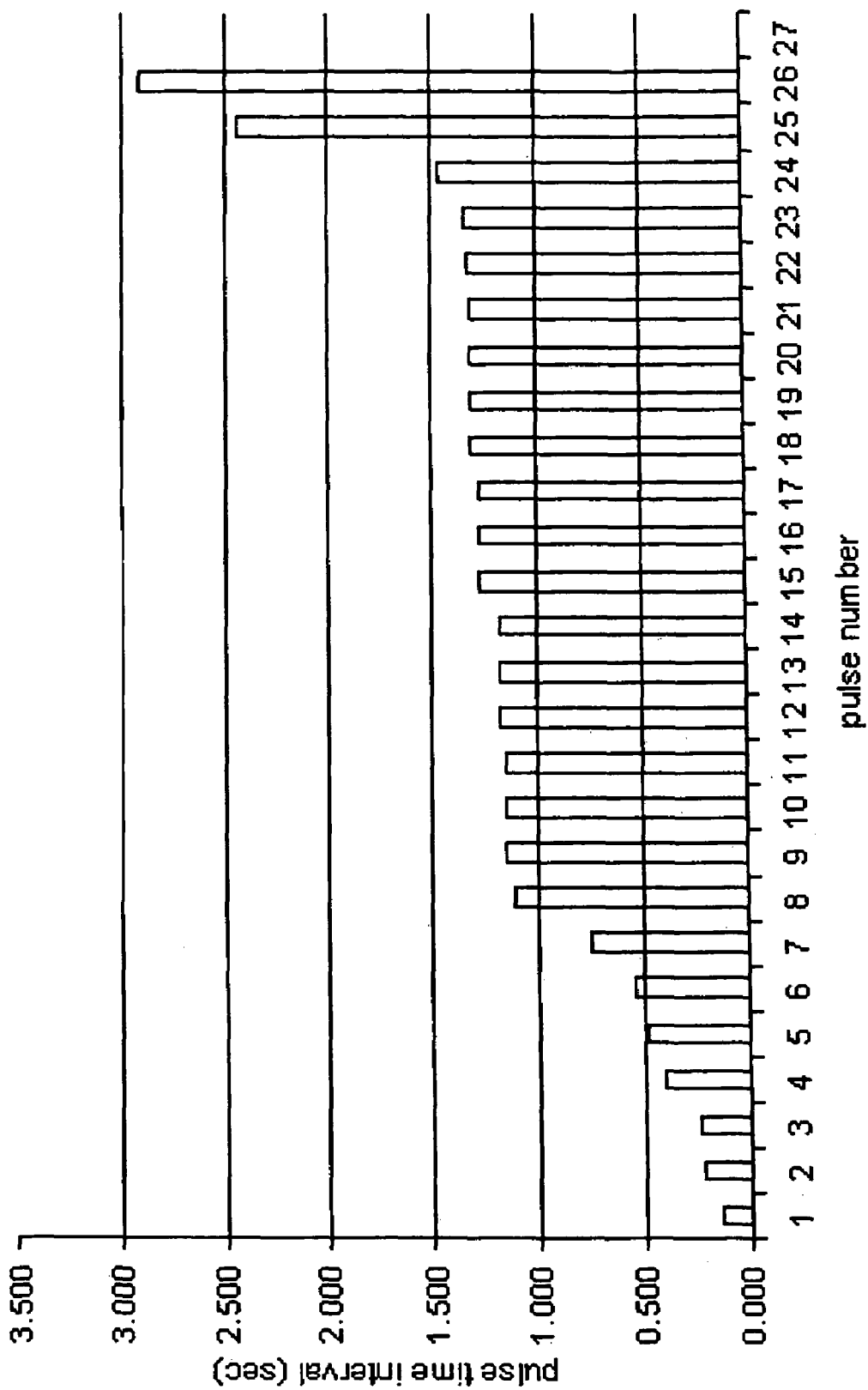
FIG. 8 is a graph showing time intervals for the rhythm shown in FIG. 7 sorted as in Method II.
Figure 9:
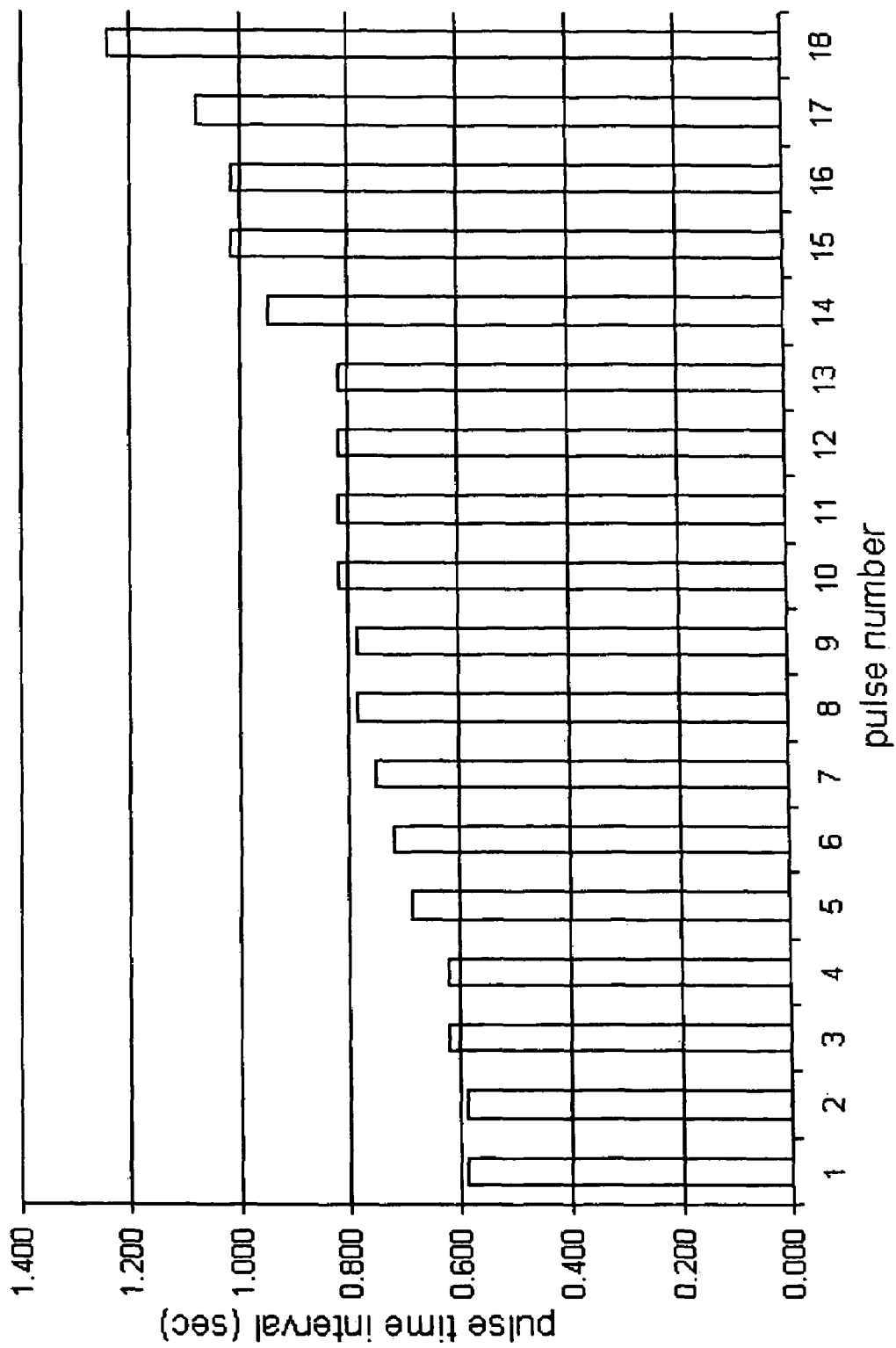
FIG. 9 is a graph showing pulse beat time intervals for atrial fibrillation sorted as in Method II.

In a second preferred method of the present invention (FIG. 2), all pulse time intervals recorded by the device are sorted from shortest interval to longest interval or vice versa. Specifically, all the time intervals recorded by the sphygmomanometer are sorted from the shortest interval to longest interval. (See FIGS. 7 and 8). Beginning with the shortest interval, the first three time intervals are used to calculate a mean and standard deviation. (See FIG. 6). The ratio of the standard deviation to the mean is the irregularity index for these three intervals. If this irregularity index is less than about 0.01, that is used as an indication that these three intervals are almost equal. The value 0.01 is therefore a threshold value, and instead of 0.01, it may be within a range of about 0.01 to about 0.03. The time interval following the shortest interval is then used to calculate an irregularity index for the next three beats. This is continued for the next time interval until the irregularity index for the three longest time intervals is calculated. If about 50% or more of the irregularity indices are less than about 0.01, then the rhythm is considered regular or an absence of atrial fibrillation, and if less than about 50% of the irregularity indices are less than about 0.01, then the rhythm is considered atrial fibrillation. (See FIG. 9 for irregularity). The value 50% is considered a cutoff value, and may be within a range of 30% to 70% (0.30 to 0.70). When this algorithm was applied to the 247 irregular readings from the study mentioned above, all the patients with atrial fibrillation were still detected as irregular while two-thirds of the previously irregular readings are now classified as regular. This results in a specificity of about 94% with a sensitivity remaining at about 100%. FIG. 2 is a flow chart schematic of the method described herein.

There is another embodiment of the invention in which the pulse rate is monitored through changes in light transmitted through a body appendage, such as a finger. Light is transmitted by a light source through the finger, or other appendage of an individual, and is received by a detector, which measures the change in light transmitted through the appendage to detect a pulse beat. The detector may comprise a conventional pulse measurement device. The detector delivers the time of each measured pulse to the processor, which carries out the operations described above. A light power supply detector sensitivity adjuster may be used to adjust the sensitivity of the detector in a known manner with respect to detecting the light from the light source. To detect the pulse beat, the finger or other appendage is placed between the light source and the detector and the light source is activated to shine light through the finger to reach the detector.

Advantageously, the invention provides a method and apparatus that easily detect the presence of irregular heartbeats from a plurality of heartbeats, pulses or other measurements.

As a further advantage, the invention differentiates atrial fibrillation from non-atrial fibrillation rhythms including normal and other abnormal rhythms.

A still further advantage is that the invention provides relatively simple, non-invasive home monitoring.

An apparatus and method is encompassed by the invention to include means for sorting the pulse beat intervals by length from shortest to longest or longest to shortest; means for calculating an irregularity index $I_1$ for the first n time intervals, the irregularity index $I_1$ being a quotient of a mean and a standard deviation of a first n time intervals; means for calculating an irregularity index $I_2$ for the n time intervals beginning with the second time interval, the irregularity index $I_2$ being a quotient of a mean and a standard deviation of n time intervals beginning with the second time interval; means for continuing to calculate an irregularity index $I_m$ where m ranges from one until N−(n−1), where N is the total number of pulse intervals; means for determining what percent, P, of the said irregularity indices $I_1, I_2, \ldots I_{N-(n-1)}$, are less than a threshold value T to determine possible atrial fibrillation in that if P exceeds a cutoff value $P_{cutoff}$, the rhythm is not atrial fibrillation and if P is less than or equal to $P_{cutoff}$, the rhythm is atrial fibrillation.

Although the present invention has been described in relation to particular embodiments thereof, many other variations and modifications and other uses may become apparent to those skilled in the art. It is preferred, therefore, that the present invention be limited not by this specific disclosure herein, but only by the appended claims.

What is claimed is:

1. A method of determining possible atrial fibrillation, said method comprising:
   detecting a sequence of pulse beats to provide a succession of time intervals corresponding to the sequence of pulse beats;
   ascertaining a mean of the succession of time intervals;
   determining lower and upper boundary values of the time intervals each as a respective percent of the mean;
   recalculating the mean based on only the time intervals that are at or between the upper and lower boundary values and not based on the time intervals that are less than the lower boundary value or higher than the upper boundary value;
   calculating a standard deviation based on only the time intervals that are at or between the upper and lower boundary values and not based on the time intervals that are less than the lower boundary value or higher than the upper boundary value; and
   determining possible atrial fibrillation based upon a quotient formed by dividing the standard deviation by the recalculated mean and comparing the quotient with a threshold value; if the quotient exceeds the threshold value, the rhythm is atrial fibrillation.

2. The method of claim 1, wherein the lower boundary value is in a range of about 0.50 to about 0.90 times the mean and the upper boundary value is in a range of 1.1 to 1.5 times the mean.

3. The method of claim 1, wherein said threshold value is within the range of 0.01 to 0.10.

4. The method of claim 1, wherein the detecting of the sequence of pulse beats is carried out by using either a sphygmomanometer or a plethysmograph.

5. A method of determining rhythms that are not atrial fibrillation, said method comprising:
   detecting a sequence of pulse beats to provide a succession of time intervals corresponding to the sequence of pulse beats;
   ascertaining a mean of the succession of time intervals;
   determining lower and upper boundary values of the time intervals each as a respective percent of the mean;
   recalculating the mean based on only the time intervals that are at or between the upper and lower boundary values and not based on the time intervals that are less than the lower boundary value or higher than the upper boundary value;
   calculating a standard deviation based on only the time intervals that are at or between the upper and lower boundary values and not based on the time intervals that are less than the lower boundary value or higher than the upper boundary value; and
   determining possible atrial fibrillation based upon a quotient formed by dividing the standard deviation by the recalculated mean and comparing the quotient with a threshold value; if the quotient is less than the threshold value, the rhythm is not atrial fibrillation.

6. The method of claim 5, where the lower boundary value is in a range of about 0.50 to about 0.90 times the mean and the upper boundary value is in a range of 1.1 to 1.5 times the mean.

7. The method of claim 5, wherein said threshold value is within the range of 0.01 to 0.10.

8. The method of claim 5, wherein the detecting of the sequence of pulse beats is carried out by using either a sphygmomanometer or a plethysmograph.

9. A method of determining possible atrial fibrillation, said method comprising:
   sorting a sequence of time intervals between pulse beats by length from shortest to longest or longest to shortest;
   determining N where N is the number of time intervals between successive pulse beats;
   calculating a first irregularity index $I_1$ for a first n time intervals of the sorted time intervals, the first n time intervals including a first time interval and at least one additional time interval, the first irregularity index $I_1$ being a quotient of a mean and a standard deviation of the first n time intervals, wherein n is less than N;
   calculating a second irregularity index $I_2$ for a second n time intervals of the sorted time intervals beginning with a second time interval, the second n time intervals including the second time interval and at least one additional time interval, the second irregularity index $I_2$ being a quotient of a mean and a standard deviation of the second n time intervals beginning with the second time interval;
   continuing to calculate an additional irregularity index $I_m$ of the sorted time intervals for each additional n time intervals in the same manner where m ranges from three until N−(n−1); and
   determining possible atrial fibrillation based on what percent, P, of the irregularity indices $I_1, I_2, \ldots I_{N-(n-1)}$, are less than a threshold value T in that if P exceeds a cutoff value, $P_{cutoff}$, then the rhythm is considered to show an absence of atrial fibrillation, and if P is less than or equal to the cutoff value, $P_{cutoff}$, then the rhythm is considered atrial fibrillation.

10. The method of claim 9, wherein said threshold value T is within the range of about 0.01 to about 0.03.

11. The method of claim 9, wherein said cutoff value, $P_{cutoff}$, is within the range of 0.30 to 0.70.

12. An apparatus to determine possible atrial fibrillation, comprising:
- means for ascertaining a mean of a succession of time intervals corresponding to that of a sequence of pulse beats;
- means for determining lower and upper boundary values of the time intervals as a respective percent of the mean;
- means for recalculating a mean of only the time intervals that are at or between the lower and upper boundary values and not the time intervals that are less than the lower boundary value or higher than the upper boundary value and for calculating a standard deviation of only the time intervals that are at or between the lower and upper boundary values and not time intervals that are less than the lower boundary value or higher than the upper boundary value; and
- means for determining possible atrial fibrillation based upon a quotient formed by dividing said standard deviation by said recalculated mean and for comparing the quotient with a threshold value.

13. The apparatus of claim 12, further comprising a detector that detects a sequence of pulse beats corresponding to the succession of pulse time intervals.

14. The apparatus of claim 13, wherein the detector is a sphygmomanometer or a plethysmograph.

15. The apparatus of claim 12, wherein the lower boundary value is in a range of about 0.50 to about 0.90 times the mean and the upper boundary value is in a range of 1.1 to 1.5 times the mean.

16. The apparatus of claim 12, wherein said threshold value is within the range of 0.01 to 0.10.

17. An apparatus to determine possible atrial fibrillation, comprising:
- means for sorting time intervals between pulse beats by length from shortest to longest or longest to shortest;
- means for determining N where N is the number of time intervals between successive pulse beats;
- means for calculating a first irregularity index $I_1$ for a first n time intervals of the sorted time intervals, the first n time intervals including a first time interval and at least one additional time interval, the first irregularity index $I_1$ being a quotient of a mean and a standard deviation of the first n time intervals, wherein n is less than N;
- means for calculating a second irregularity index $I_2$ for a second n time intervals of the sorted time intervals beginning with a second time interval, the second n time intervals including the second time interval and at least one additional time interval, the second irregularity index $I_2$ being a quotient of a mean and a standard deviation of the second n time intervals beginning with the second time interval;
- means for continuing to calculate an additional irregularity index $I_m$ of the sorted time intervals for each additional n time intervals in the same manner where m ranges from three until $N-(n-1)$; and
- means for determining possible atrial fibrillation based on what percent, P, of the irregularity indices $I_1, I_2, \ldots I_{N-(n-1)}$, are less than a threshold value T in that if P exceeds a cutoff value, $P_{cutoff}$, then the rhythm is not atrial fibrillation, and if P is less than or equal to the cutoff value, $P_{cutoff}$, then the rhythm is atrial fibrillation.

* * * * *